United States Patent
Honda et al.

(10) Patent No.: US 9,636,123 B2
(45) Date of Patent: May 2, 2017

(54) CALCULUS RETRIEVING/REMOVING DEVICE AND METHOD

(71) Applicant: TERUMO KABUSHIKI KAISHA, Tokyo (JP)

(72) Inventors: Kei Honda, Hadano (JP); Makoto Narita, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 126 days.

(21) Appl. No.: 14/620,671

(22) Filed: Feb. 12, 2015

(65) Prior Publication Data
US 2015/0265295 A1 Sep. 24, 2015

Related U.S. Application Data

(63) Continuation of application No. 14/221,858, filed on Mar. 21, 2014.

(51) Int. Cl.
*A61B 17/221* (2006.01)
*A61B 17/22* (2006.01)

(52) U.S. Cl.
CPC ........ *A61B 17/22* (2013.01); *A61B 17/22031* (2013.01); *A61B 2017/22079* (2013.01); *A61B 2017/22084* (2013.01)

(58) Field of Classification Search
CPC .............. A61B 17/22; A61B 17/22031; A61B 17/22032; A61B 17/221; A61B 2017/22051; A61B 2017/22052; A61B 2017/22054; A61B 2017/22055; A61B 2017/22062; A61B 2017/22064;
(Continued)

(56) References Cited

U.S. PATENT DOCUMENTS 4,696,297 A * 9/1987 Pleines ................ A61B 17/22
                                                          606/22
5,338,294 A    8/1994 Blake, III
(Continued)

FOREIGN PATENT DOCUMENTS

FR    1 460 776        1/1966
JP    2013-183951 A    9/2013

OTHER PUBLICATIONS

U.S. Appl. No. 14/221,954, filed Mar. 21, 2014, Kei Honda et al.
(Continued)

*Primary Examiner* — Ryan J Severson
(74) *Attorney, Agent, or Firm* — Buchanan Ingersoll & Rooney PC

(57) ABSTRACT

A calculus removing device includes an elongated member and a retrieval part fixed to the elongated member. A discharge force is produced in a lumen in the elongated member to discharge fluid in the lumen into the renal pelvis, and a suction force is produced in the lumen to draw fluid into the lumen from the renal pelvis. An outlet communicates with the lumen, and fluid in the lumen is discharged into the renal pelvis through the outlet in the presence of the discharge force. An inlet communicates with the lumen, and fluid in the renal pelvis is drawn into the lumen through the inlet in the presence of the suction force. The retrieval part includes an interior that communicates with the lumen and the renal pelvis, and the interior is configured to receive the calculus in the renal pelvis in the presence of the suction force.

20 Claims, 16 Drawing Sheets

(58) Field of Classification Search
CPC ........... A61B 2017/22065; A61B 2017/22067; A61B 2017/22072; A61B 2017/22079; A61B 2017/22081; A61B 2017/22082; A61B 2017/22084; A61B 2017/2212; A61B 2017/2217; A61B 2217/007
See application file for complete search history.

(56) References Cited

U.S. PATENT DOCUMENTS

| | | | | |
|---|---|---|---|---|
| 6,544,227 B2* | 4/2003 | Sahatjian | ......... | A61B 17/22012 604/113 |
| 6,565,530 B2* | 5/2003 | Sahatjian | ......... | A61B 17/22012 604/113 |
| 6,663,594 B2* | 12/2003 | Sahatjian | ......... | A61B 17/22012 604/113 |
| 6,692,484 B1* | 2/2004 | Karpiel | ............ | A61B 17/22031 600/31 |
| 6,866,651 B2* | 3/2005 | Constantz | .............. | A61B 17/22 514/891 |
| 7,101,379 B2* | 9/2006 | Gregory, Jr. | ......... | A61B 17/221 606/127 |
| 7,137,966 B2* | 11/2006 | Sahatjian | ......... | A61B 17/22012 604/113 |
| 7,731,722 B2* | 6/2010 | Lavelle | ................ | A61B 17/221 606/127 |
| 7,837,672 B2* | 11/2010 | Intoccia | ................. | A61B 17/22 604/101.01 |
| 7,906,152 B2* | 3/2011 | Constantz | .............. | A61B 17/22 424/666 |
| 7,963,944 B2* | 6/2011 | Sahatjian | ......... | A61B 17/22012 604/113 |
| 8,197,463 B2* | 6/2012 | Intoccia | ................. | A61B 17/22 604/101.01 |
| 8,372,037 B2* | 2/2013 | Sahatjian | ......... | A61B 17/22012 604/113 |
| 8,394,059 B2* | 3/2013 | Sahatjian | ......... | A61B 17/22012 604/113 |
| 8,409,218 B2* | 4/2013 | Schwarz | .......... | A61B 17/12022 600/420 |
| 8,409,237 B2* | 4/2013 | Galdonik | ............... | A61B 17/22 606/200 |
| 8,679,059 B2* | 3/2014 | Sahatjian | ......... | A61B 17/22012 604/113 |
| 8,834,416 B2* | 9/2014 | Sahatjian | ......... | A61B 17/22012 604/113 |
| 8,998,928 B2* | 4/2015 | Schwarz | .......... | A61B 17/12022 600/430 |
| 2002/0119116 A1* | 8/2002 | Sahatjian | ......... | A61B 17/22012 424/78.31 |
| 2002/0120237 A1* | 8/2002 | Sahatjian | ......... | A61B 17/22012 604/180 |
| 2003/0088254 A1* | 5/2003 | Gregory, Jr. | ......... | A61B 17/221 606/127 |
| 2003/0178030 A1* | 9/2003 | Constantz | .............. | A61B 17/22 128/898 |
| 2003/0195464 A1* | 10/2003 | Sahatjian | ......... | A61B 17/22012 604/113 |
| 2003/0229332 A1* | 12/2003 | Intoccia | ................. | A61B 17/22 604/508 |
| 2004/0019358 A1* | 1/2004 | Kear | ................ | A61B 17/22031 606/127 |
| 2005/0043756 A1* | 2/2005 | Lavelle | ................ | A61B 17/221 606/200 |
| 2005/0053662 A1* | 3/2005 | Sahatjian | ......... | A61B 17/22012 424/486 |
| 2005/0143678 A1* | 6/2005 | Schwarz | .......... | A61B 17/12022 601/4 |
| 2005/0251104 A1* | 11/2005 | Constantz | .............. | A61B 17/22 604/514 |
| 2005/0277976 A1* | 12/2005 | Galdonik | ............... | A61B 17/22 606/200 |
| 2006/0129091 A1 | 6/2006 | Bonnette et al. | | |
| 2006/0189921 A1* | 8/2006 | Galdonik | ............... | A61B 17/22 604/27 |
| 2006/0233891 A1* | 10/2006 | Constantz | .............. | A61B 17/22 424/666 |
| 2007/0066933 A1* | 3/2007 | Sahatjian | ......... | A61B 17/22012 604/23 |
| 2007/0088256 A1* | 4/2007 | Intoccia | ................. | A61B 17/22 604/102.02 |
| 2008/0103481 A1* | 5/2008 | Vogel | ............... | A61B 17/12022 604/514 |
| 2008/0188866 A1* | 8/2008 | Karpiel | ............ | A61B 17/22032 606/127 |
| 2010/0274231 A1* | 10/2010 | Pravong | ................. | A61B 17/22 606/2.5 |
| 2011/0060256 A1* | 3/2011 | Schwarz | .......... | A61B 17/12022 601/4 |
| 2011/0092957 A1* | 4/2011 | Intoccia | ................. | A61B 17/22 604/540 |
| 2011/0245801 A1* | 10/2011 | Sahatjian | ......... | A61B 17/22012 604/506 |
| 2012/0010595 A1* | 1/2012 | Sahatjian | ......... | A61B 17/22012 604/506 |
| 2013/0131445 A1* | 5/2013 | Zerfas | .................... | A61B 17/22 600/104 |
| 2013/0150789 A1* | 6/2013 | Sahatji | ............. | A61B 17/22012 604/131 |
| 2013/0172789 A1* | 7/2013 | Schwarz | .......... | A61B 17/12022 601/4 |
| 2013/0231676 A1* | 9/2013 | Sahatjian | ......... | A61B 17/22012 606/127 |
| 2015/0265294 A1* | 9/2015 | Honda | .................... | A61B 17/22 606/128 |
| 2015/0265295 A1* | 9/2015 | Honda | .................... | A61B 17/22 606/127 |
| 2015/0265296 A1* | 9/2015 | Honda | .................... | A61B 17/22 606/127 |
| 2015/0265297 A1* | 9/2015 | Honda | .................... | A61B 17/22 606/127 |
| 2015/0265298 A1* | 9/2015 | Honda | .................... | A61B 17/22 606/127 |
| 2016/0015393 A1* | 1/2016 | Schwarz | .......... | A61B 17/12022 601/4 |

OTHER PUBLICATIONS

U.S. Appl. No. 14/222,021, filed Mar. 21, 2014, Kei Honda.
Communication pursuant to Article 94(3) EPC dated Jun. 23, 2016 issued by the European Patent Office in corresponding European Patent Application No. 15 159 014.8 (6 pages).
Extended European Search Report dated Jun. 15, 2015 issued by the European Patent Office in corresponding European Patent Application No. 15 159 014.8 (8 pages).

* cited by examiner

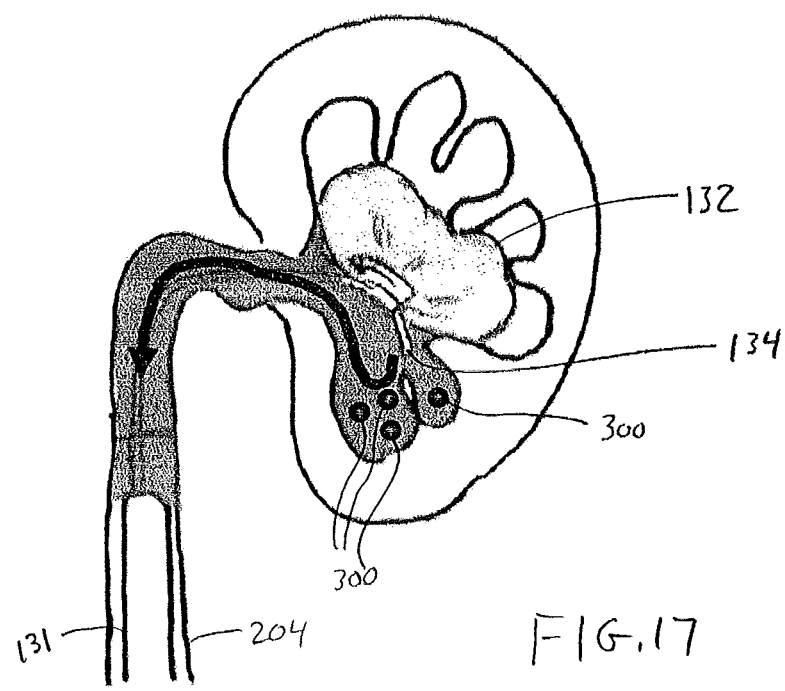
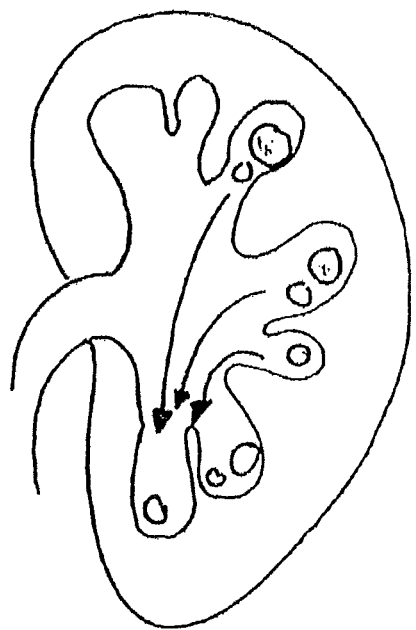
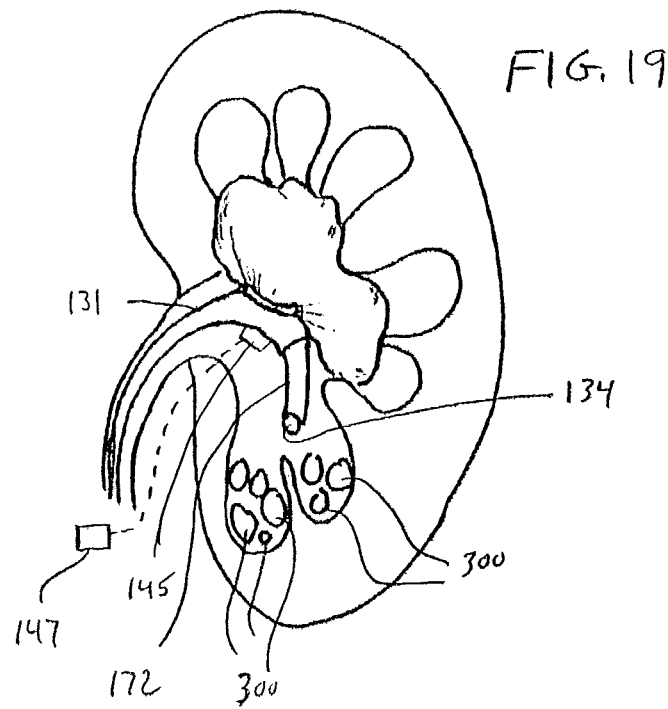

CALCULUS RETRIEVING/REMOVING DEVICE AND METHOD

This application is a continuation of U.S. application Ser. No. 14/221,858 filed on Mar. 21, 2014, the entire content of which is incorporated herein by reference.

TECHNICAL FIELD

The present invention generally pertains to methods and systems for retrieving/removing a mass from a human body. More specifically, the invention involves methods and systems for retrieving/removing calculus (e.g., stones) from a portion of a human body such as the renal pelvis or the ureter.

BACKGROUND DISCUSSION

The term urinary calculus (e.g., kidney stones and ureteral stones) refers to masses or stones, typically solid particles, that form in the human body and are located in the kidneys and/or the ureter. They can exhibit a variety of chemical compositions including calcium oxalate, calcium phosphate, uric acid, cystine, and struvite.

Stone disease (e.g., kidney stones and ureteral stones) is a relatively common urological disorder. The presence of calculus in the body can manifest itself in a variety of ways and can produce a number of medical ailments. For example, the presence of calculus in the renal pelvis (kidney) can cause blood in the urine, urinary obstruction, infection, and various degrees of pain ranging from vague frank pain to much more severe pain not capable of being relieved through general pain medication. The presence of stones or calculus in the ureter can result in relatively severe side and back pain, pain below the ribs, and pain that sometimes spreads to the lower abdomen and groin, as well as pain during urination and hematuria.

Fortunately, many calculus or stones pass out of the body without requiring any specific medical intervention. In those situations where the calculus does not naturally pass out of the body, a medical procedure may be required. Known medical procedures typically fall into three categories.

In the past, three main treatments have been used to address calculus or kidney stones. These include shock wave lithotripsy (ESWL), transurethral lithotripsy or ureteroscopy (URS), and percutaneous nephrouretero lithotripsy (PCNL) which is sometimes also referred to as percutaneous nephrolithotomy (PCN).

Shock wave lithotripsy is performed as an extracorporeal treatment. This treatment utilizes a machine called a lithotripter that operates by directing ultrasonic or shock waves from outside the body, through the skin and tissue, and at the calculus or stones. Repeated shock waves apply stress to the stones, eventually breaking the individual stones into smaller pieces which can more easily pass through the urinary tract in urine. One benefit associated with shock wave lithotripsy is that it is a rather simple procedure. But it has been found that there is a relatively high rate of kidney stone recurrence following shock wave lithotripsy.

Transurethral lithotripsy or ureteroscopy represents one such alternative form of treatment. This treatment involves the use of small fiber optic instrument called a ureteroscope which allows access to the calculus in the ureter or kidney. The ureteroscope can be a rigid ureteroscope or more commonly, a flexible ureteroscope. The ureteroscope allows the medical professional to visualize the stone as the ureteroscope moves along the ureter or enters the kidney by way of the bladder and the urethra. Once the calculus is visualized, a basket-like device is used to grasp smaller stones and remove them. If the calculus is excessively large to remove as a single piece, it can be broken into a smaller pieces by using laser energy.

The third form of treatment is percutaneous nephrolithotomy. This procedure is often used with relatively larger calculus that cannot be effectively treated with either ESWL or URS. Percutaneous nephrolithotomy involves nephrostomy; making an incision at the appropriate location, needling by paracentesis needle, positioning a guide wire through the paracentesis needle's lumen into the kidney under radiographic guidance, and then expanding perforated site. A nephroscope is then moved into the kidney via nephrostomy to visualize the calculus. Fragmentation of the calculus can be performed using an ultrasonic probe or laser.

Though these procedures have been commonly used, they are susceptible of certain short comings. For example, the ESWL procedure results in a relative large number of small calculus or small stones, while other procedures require a relatively narrow and long access route or are difficult to implement due to the inability to accurately capture the stones. In addition to, many crush pieces should be removed one by one in URS and PCNL procedure. The procedure time can also be excessively long, and can result in a relatively low "stone free rate." The recurrence rate can also be unacceptably high. And the potential patient complications (e.g., ischemia of the ureter, obstruction of ureter, back-flow and/or high-stress to the renal pelvis, infection of the urinary tract, and other possible injury) can be undesirably high.

SUMMARY

According to one aspect, a calculus retrieving device for retrieving calculus in a renal pelvis comprises: an elongated member possessing a longitudinal extent and including a lumen extending along the longitudinal extent of the elongated member; a plunger positioned in the lumen of the elongated member and axially movable in a forward direction and a rearward direction along the lumen of the elongated member; and an enclosure fixed to the elongated member at a distal end portion of the elongated member so that the elongated member and the enclosure are movable together as a unit, with the elongated member and the enclosure together being sized to be positioned in a renal pelvis. An outlet is in selective communication with the lumen and fluid in the lumen is discharged through the outlet into the renal pelvis during axial movement of the plunger in the forward direction, and an inlet is in selective communication with the lumen and fluid in the renal pelvis is drawn into the lumen through the inlet during axial movement of the plunger in the rearward direction. The enclosure encloses an interior configured to receive the calculus in the renal pelvis that is drawn toward the inlet together with the fluid in the renal pelvis during the axial movement of the plunger in the rearward direction.

According to another aspect, a calculus retrieving device for retrieving calculus in a renal pelvis comprises an elongated member and a retrieval part fixed to the elongated member so that the elongated member and the retrieval part are movable together as a unit, with the elongated member and the retrieval part together being sized to be positioned in the renal pelvis. The elongated member includes a lumen in which is produced a discharge force to discharge fluid in the lumen out of the elongated member and into the renal pelvis and in which is produced a suction force to draw fluid into the lumen from the renal pelvis. An outlet is in selective communication with the lumen in the elongated member, and fluid in the lumen is discharged through the outlet and into the renal pelvis by the discharge force in the lumen of the elongated member, and an inlet is in selective communication with the lumen in the elongated member, and fluid in the renal pelvis is drawn through the inlet and into the lumen by the suction force in the lumen of the elongated member. The retrieval part includes an interior that communicates with the lumen and that communicates with the renal pelvis when the calculus removing device is in the renal pelvis. The interior of the elongated member is configured to receive the calculus in the renal pelvis when the suction force is produced in the lumen of the elongated member.

Other features and aspects of the calculus retrieving/removing device and method disclosed here will become more apparent from the following detailed description considered with reference to the accompanying drawing figures in which like elements are designated by like reference numerals.

BRIEF DESCRIPTION OF DRAWINGS

FIG. 17 is a schematic illustration of the elongated member shown in FIG. 16 positioned in a renal pelvis.

FIG. 18 is a schematic illustration of a renal pelvis illustrating an aspect of the method in which calculus in one portion of the renal pelvis are moved to another portion of the renal pelvis.

FIG. 19 is a schematic illustration of the calculus removing/retrieving device shown in FIG. 16 positioned in the renal pelvis after the calculus has been moved from the one portion of the renal pelvis to the other portion of the renal pelvis.

DETAILED DESCRIPTION

Figure 1:
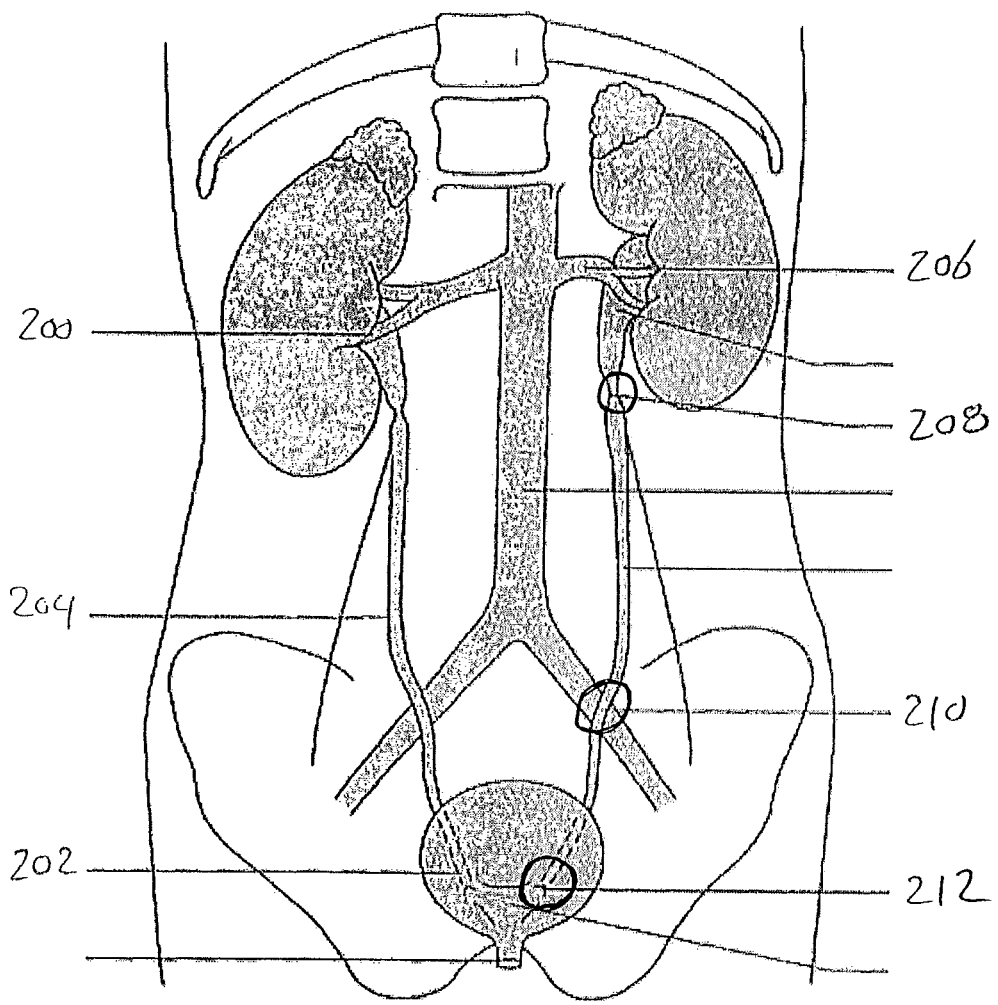
FIG. 1 is a schematic illustration of a portion of the human anatomy, including the urinary tract.
Figure 2:
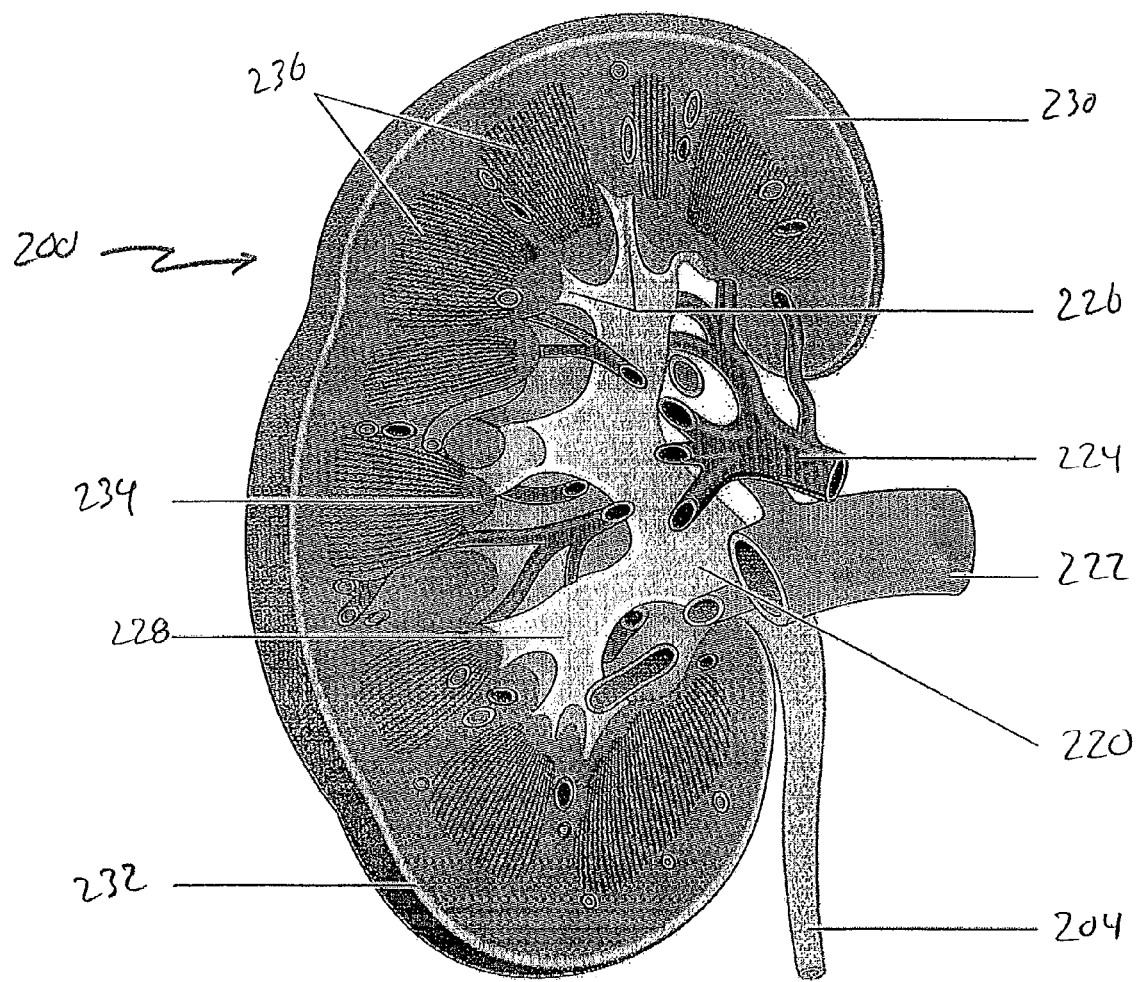
FIG. 2 is a schematic cross-sectional view of a kidney.

Before discussing details and aspects of the methods and calculus removing/retrieving device described here as examples of the invention disclosed here, reference is made to FIGS. 1 and 2 to describe anatomical aspects of relevant aspects of a human body, including the urinary tract. Referring first to FIG. 1, the urinary tract includes the kidney 200, the bladder 202 and the ureter 204. The ureter 204 extends between and is connected to both the kidney 200 and the bladder 202. The ureter 204 possesses a lumen (ureteral lumen) that communicates with the interior of the kidney 200 and the interior of the bladder 202. The terminal end portion of the ureter penetrates through the muscle wall of bladder, and opens into the inside of the bladder at the ureteral orifice. Additional features illustrated in FIG. 1 include the physiological stricture of the ureter 204, the ureteropelvic junction (UPJ) 208, the iliac artery crossing 210 and the ureterovesical junction (ureter bladder junction (UBJ)) 212.

FIG. 2 illustrates additional details associated with the kidney 200. The identified parts of the kidney in FIG. 2 include the renal pelvis 220, the renal vein 222, the renal artery 224, several of the minor calyces 226, one of the major calyx 228, the cortex 230, the capsule 232, the papilla of medulla 234 and the medulla (pyramids) 236.

The methods and devices disclosed here for removing/retrieving calculus have particularly useful application to address calculus located in the ureter 204 (ureter stones) and calculus located in the renal pelvis 220 (kidney stones).

Figure 3:
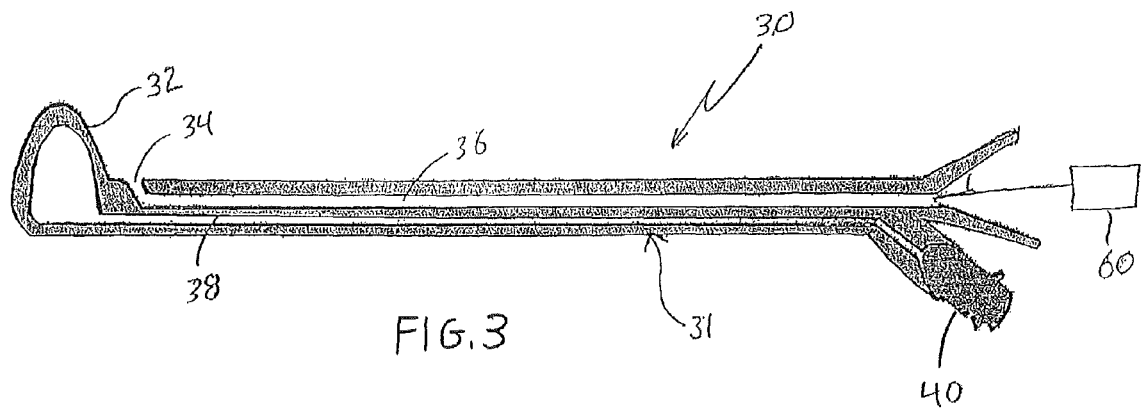
FIG. 3 is a longitudinal cross-sectional view of a calculus removing/retrieving device representing one example of the device disclosed here used to carry out an aspect of the disclosed method.

A first embodiment of the calculus removing/retrieving device disclosed here is illustrated in FIG. 3. The calculus removing/retrieving device 30 includes an elongated member 31 having a ureter plug part 32 and an irrigation port or irrigation nozzle 34. The ureter plug part 32 is configured to be expanded to a relatively larger size as shown in FIG. 3 and contracted to a relatively smaller size. The ureter plug part 32 is thus configured to be enlarged and reduced in size. In the illustrated embodiment disclosed by way of example, the ureter plug part 32 is an inflatable balloon. The ureter plug part 32 is expanded by introducing a fluid into the interior of the ureter plug part 32, and the ureter plug part 32 is contracted by allowing the fluid to empty from the ureter plug part 32. The fluid can be water, air, contrast medium, etc.

Fluid is introduced into the ureter plug part 32 and is expelled from the ureter plug part 32 by way of a ureter plug part lumen 38. One end of the ureter plug part lumen 38 opens to the interior of the ureter plug part 32 and the opposite end of the ureter plug part lumen 38 is provided with a check valve 40. The check valve 40 can be of any known construction. One example is illustrated in FIG. 4.

Figure 4:
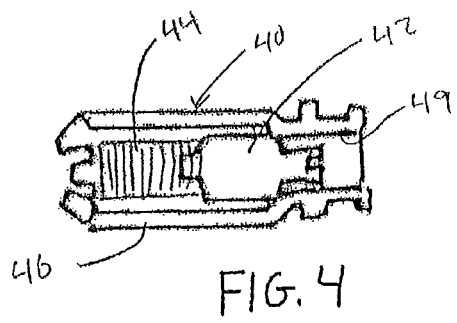
FIG. 4 is a cross-sectional view of a check valve used in the calculus removing/retrieving device shown in FIG. 3.

The check valve in FIG. 4 includes a movable rubber plug 42 and a spring 44, both of which are positioned in, and enclosed within, a housing 46. The housing 46 includes an open end 49 at one end (the right end in FIGS. 4 and 5) and a closed end (equipped with a through hole) at the opposite end (the left end in FIGS. 4 and 5). The spring 44 normally biases the rubber plug 42 in the direction of the open end 49 and into sealing engagement with the valve seat 48 of the housing 46. FIG. 4 illustrates the normally closed position of the check valve 40 in which the rubber plug 42 is in sealing engagement with the valve seat 48 of the housing 46. The check valve 40 is configured to be opened by moving the rubber plug 42 against the biasing force of the spring 44 (i.e., to the left in FIGS. 4 and 5). In the illustrated embodiment, this is accomplished by inserting the tip end portion of a syringe 50 into the open end 49 of the housing 46. Inserting the tip end portion of the syringe 50 into the open end 49 of the housing 46 causes the tip end of the syringe 50 to contact the rubber plug 42. Pushing the syringe 50 further inward overcomes the biasing force of the spring 44 and urges the rubber plug 42 out of engagement with valve seat 48. This thus opens the check valve 40. Next, by forwardly moving the plunger 52 within the barrel of the syringe, air in the barrel of the syringe is introduced into the ureter plug part lumen 38 to thus inflate or expand the ureter plug part 32.

Figure 6:
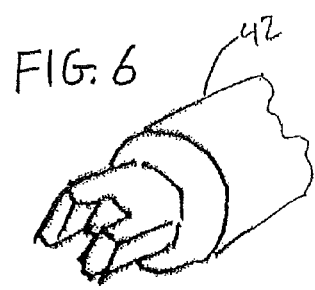
FIG. 6 is a perspective view of the end portion of the rubber plug used in the check valve shown in FIGS. 4 and 5.

FIG. 6 illustrates the end portion of the rubber plug 42 that faces and is contacted by the tip end of the syringe 50. As illustrated, the end portion of the rubber plug 42 possesses a forked configuration in which the center region is cut-out (i.e., a U-shaped cut-out). This allows the fluid inside the barrel of the syringe 50 to be discharged from the tip end of the syringe when the tip end of the syringe is in contact with the rubber plug 42. After an appropriate amount of fluid is introduced into the ureter plug part 32 to expand or inflate the ureter plug part 32, the syringe 50 can be disengaged from the check valve 40. At such time, the spring 44 biases the rubber plug 42 back into engagement with the valve seat 48 to close the check valve 40. The ureter plug part 32 thus remains in the expanded or inflated state. Naturally, the ureter plug part 32 can be contracted by the reverse method to that described above.

The irrigation lumen 36 is connected to a fluid source 60. The fluid source 60 is preferably a liquid, more preferably saline. In a more preferable example, the cross-sectional area of the irrigation lumen 36 is larger than the cross-sectional area of the ureter plug part lumen 38, because efficient irrigation needs a relatively high flow rate, but efficient inflation does not require such a high flow rate.

Figure 7:
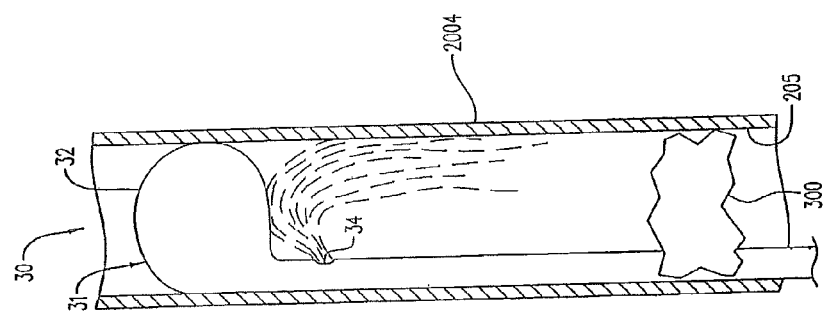
FIG. 7 is a schematic illustration of the calculus removing/retrieving device show in FIG. 3 positioned in the lumen of a ureter (ureteral lumen).

FIG. 7 is an illustration of the calculus removing/retrieving device 30 positioned in the lumen 205 of the ureter 204. In use, the calculus removing/retrieving device 30 is introduced into the ureteral lumen 205 by way of the bladder and the urethra. That is, with the ureteral plug part 32 in the contracted or deflated condition, the tip end of the calculus removing/retrieving device 30 is introduced into the urethra, is advanced through the bladder 202 and is moved along the ureter 204. The calculus removing/retrieving device 30 is moved in the forward direction in the ureter 204 to position the ureteral plug part 32 at a position beyond the calculus or stone(s) 300 to be removed. That is, the calculus removing/retrieving device is moved within the ureter 204 so that the ureteral plug part 32 moves past the calculus or stone(s) 300 to position the ureteral plug part 32 at a position between the renal pelvis (kidney) and the calculus 300.

After the ureteral plug part 32 is positioned at the appropriate place in the ureter, the ureteral lumen 205 is occluded. This occlusion is accomplished by inserting the tip end portion of the syringe 50 into the open end 49 of the valve 40 to open the valve 40, forwardly pushing the plunger 52 in the barrel of the syringe 50 to deliver fluid from the syringe barrel to the ureteral plug part 32 by way of the valve 40 and the ureteral plug part lumen 38, thus causing the ureter plug part 32 to outwardly expand as described above so that the outer surface of the expanded ureteral plug part 32 contacts the inner surface of the ureteral lumen 205. More specifically, the expanded ureteral plug part 32 preferably contacts the inter wall of the ureteral lumen 205 along a continuous circumference of the ureteral plug part 32. The expanded or inflated ureteral plug part 32 is an example of an occlusion means for occluding the ureteral lumen 205.

Once the ureteral lumen 205 is occluded as shown in FIG. 7, fluid (liquid) is discharged from the irrigation port 34 to wash the ureteral lumen 205. The fluid discharged from the irrigation port 34 flows towards the calculus 300 and then continues flowing towards the bladder. The fluid discharged into the ureteral lumen 205 by way of the irrigation port 34 carries away (flushes or washes away) the calculus 300 towards the bladder. The fluid thus washes away or flushes the calculus 300 to remove the calculus 300 from the ureteral lumen. The calculus 300 can flow out of the bladder with the urine stream naturally because the urethral lumen size is larger than the size of the calculus 300 and the ureteral lumen 205. After the discharge of the fluid is completed (i.e., after the calculus 300 has been washed away), the ureteral plug part 32 is contracted or deflated by simply pressing against the rubber plug 42 in the check valve 40 so that the rubber plug 42 lifts off the valve seat 48, thus allowing fluid to leave the ureteral plug part 32. Once the ureteral plug part 32 is deflated or contracted, the ureteral lumen 205 is no longer occluded. It is now possible to withdraw the elongated member 32 out of the ureteral lumen (i.e., away from the kidney and towards the bladder).

If the calculus or stones 300 in the ureter 204 are many, it is possible to carry-out the above-described operation in a step-wise manner. For example, when moving the ureteral plug part 32 within the ureter 204 toward the kidney, the ureteral plug part 32 can be moved past some of the calculus or stones 300, whereupon the above-described operation is carried out to flush or wash away the calculus or stones 300 downstream of the ureteral lumen 205. After such flushing, the ureteral plug part 32 is moved once again in the forward direction toward the kidney past more of the calculus or stones 300. This is repeated until all of the calculus or stones 300 have been washed out of or removed from the ureter 204. As another example or possibility, the fluid can be discharged from the irrigation port 34 while rotating the calculus removing/retrieving device 30. In this way, it is possible to more evenly discharge fluid with respect to the calculus or stones 300.

It is also possible to use the expanded or inflated ureteral plug part 32 as a "rake" to rake-out the calculus or stones 300 from the ureter and thus assist the washing or flushing by the fluid. After washing, or during washing, the partly expanded or inflated ureteral plug part 32 is moved rearwardly within the ureter 204 in the direction toward the bladder 202. The ureteral plug part 32 is moved in this way while the ureteral plug part 32 is in the expanded or inflated state so that the expanded or inflated ureteral plug part 32 pulls along or rakes the calculus or stones 300.

As a part of the operational procedures described above, it is also possible to perform lithotripsy to break-up the calculus or stones 300 using an acoustic pulse. The use and effect of lithotripsy is known in the art and so a detailed discussion is not set forth here. The lithotripsy procedure can be performed after the ureteral plug part 32 is moved/positioned beyond the calculus or stones 300, but before expanding the ureteral plug' part 32. Alternatively, the lithotripsy procedure can be performed after the ureteral plug part 32 is moved/positioned beyond the calculus or stones 300 and after expanding the ureteral plug part 32, but before discharging fluid from the irrigation port or nozzle to flush or wash the ureteral lumen 205 with the discharged fluid. It is further possible to perform lithotripsy to break-up or fragment the calculus or stones before moving the ureteral plug part 32 into the ureter 204.

Figure 9:
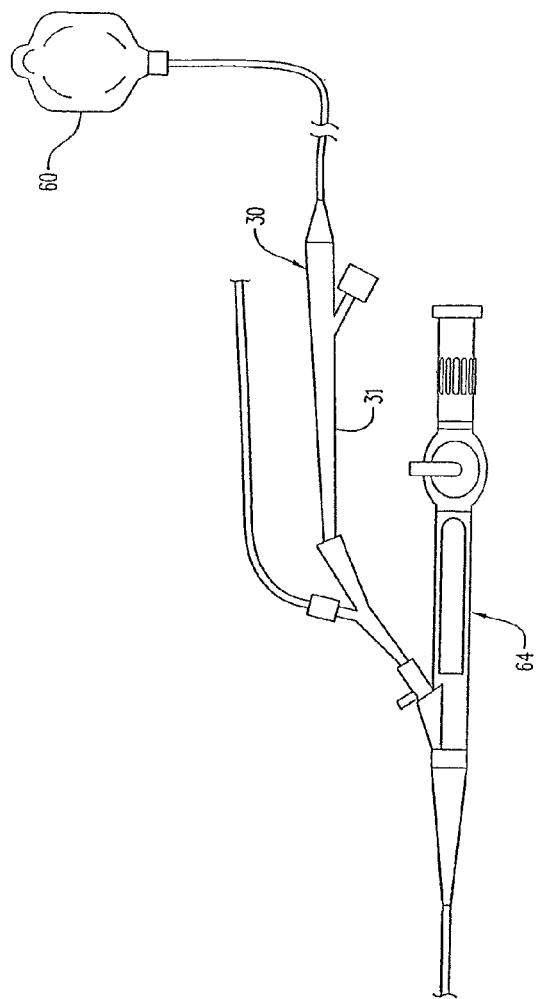
FIG. 9 is a schematic illustration of the calculus removing/retrieving device used with an ureteroscope.
Figure 8:
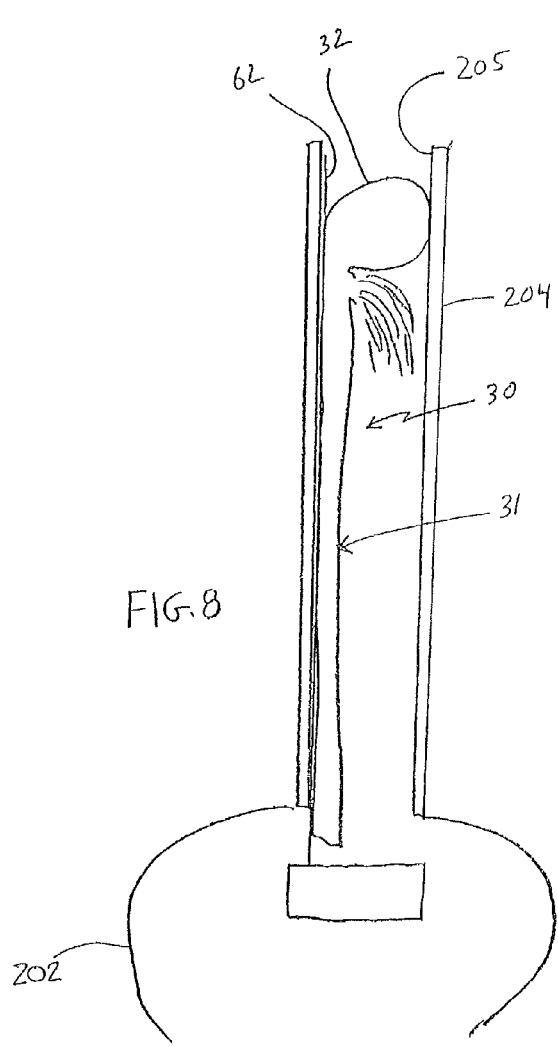
FIG. 8 is a schematic illustration of the calculus removing/retrieving device shown in FIG. 7 positioned in the ureteral lumen while being guided by a guide wire under observation with an ureteroscope.

FIG. 8 illustrates another aspect of the disclosure here involving the calculus removing/retrieving device, and associated method, shown in FIGS. 3-7. The calculus removing/retrieving device 30 may be used together with a guide wire 62. The calculus removing/retrieving device 30 may be appropriately configured in the normal way to accommodate the guide wire 62, for example by inserting the calculus removing/retrieving device in the direction toward the ureter 204 across the UBJ 212 with a guide wire 62. The guide wire 62 is then used to guide the calculus removing/retrieving device 30 to the desired location in the ureter. FIG. 9 illustrates that the calculus removing/retrieving device 30 can be used with an ureteroscope 64. This ureteroscope 64 possesses a known construction and so a detailed discussion of associated features will not be described in detail. In this version of the calculus removing/retrieving device 30 and method, the ureteroscope 64 can be a rigid ureteroscope.

In use, the guide wire 62 is appropriately introduced into the body (e.g., through the urethra) and advanced through the bladder, ureteral orifice and into the ureter 204, and the tip of the guide wire 62 enters the kidney 200 through the ureter 204. The ureteroscope 64 is then inserted into the ureter 204 along the guide wire 62. The calculus removing/retrieving device 30 is inserted into the instrument lumen in the ureteroscope 64, and then debouched into the ureter 204 from the tip or open end of the instrument lumen of the ureteroscope 64. Alternatively, the calculus removing/retrieving device 30 may be inserted into the instrument lumen in the ureteroscope 64 first. Then the calculus removing/retrieving device 30 and the ureteroscope 64 are inserted into the ureter 204 along the guide wire 62 together. The ureteroscope 64 provides a mechanism for visually observing the calculus in the ureter to appropriately position the calculus removing/retrieving device relative to the calculus, including advancing the ureteral plug part 32 to a position beyond the calculus (i.e., between the kidney and the calculus). The procedure discussed above for discharging fluid (liquid) into the ureter to wash or flush the ureter lumen and the calculus or stones is then followed.

In the operation discussed above, after the calculus removing/retrieving device 30 is properly positioned in the ureter 204, the ureteroscope 64 can be pulled-back in the rearward direction to a position outside the ureter 204 (e.g., to a position in the bladder) or the ureteroscope 64 can be pulled-back so that it is removed from the living body. That is, the ureteroscope 64 can be pulled-back to a position outside the ureter 204 or outside the body before discharging fluid from the irrigation port or nozzle to flush or wash the ureteral lumen 205 with the discharged fluid. As an alternative, after the calculus removing/retrieving device 30 is positioned at the desired place in the ureter 204, the ureteroscope 64 can be kept at its position, and pulled-back to outside the living body concurrently with the discharging of the fluid from the irrigation port or nozzle to flush or wash the ureteral lumen 205 with the discharged fluid. In this latter situation, the ureteroscope 64 is pulled-back together with the calculus and the liquid.

As discussed above, the guide wire 62 may be used to help guide the calculus removing/retrieving device 30 and/or the ureteroscope 64. The guide wire 62 can also be used to change and keep the ureter 204 shape as a straight shape. The guide wire 62 can also be used to open the ureteral orifice before the washing to facilitate draining of the fluid after the washing begins. Such shape's changes help create or maintain a drainage passage easily through the ureteral lumen 205.

Figure 10:
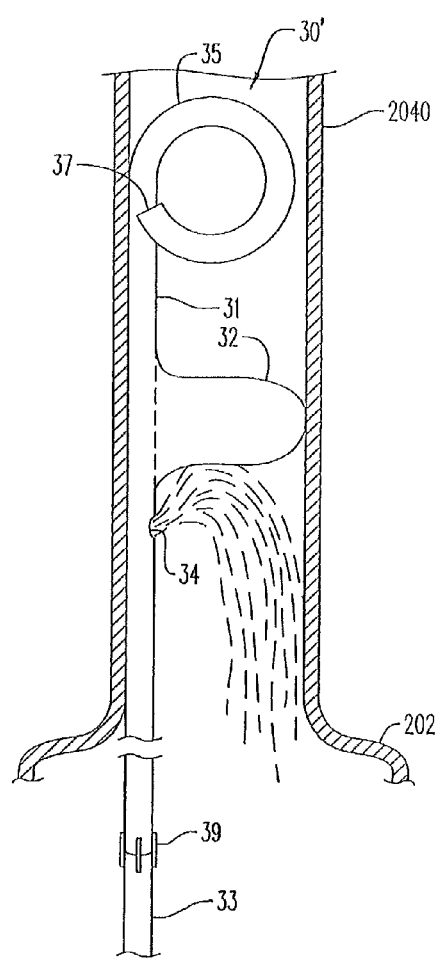
FIG. 10 is a schematic illustration of another embodiment of the calculus removing/retrieving device disclosed here by way of example and positioned in a ureteral lumen.
Figure 11:
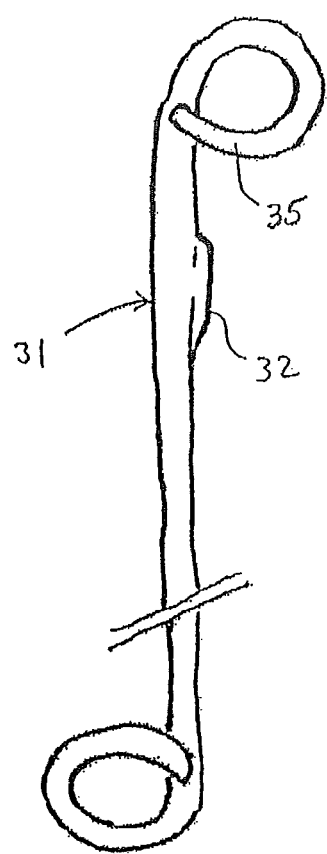
FIG. 11 illustrates the calculus removing/retrieving device shown in FIG. 10 after separation of a proximal end portion to result in a ureteral stent.
Figure 12:
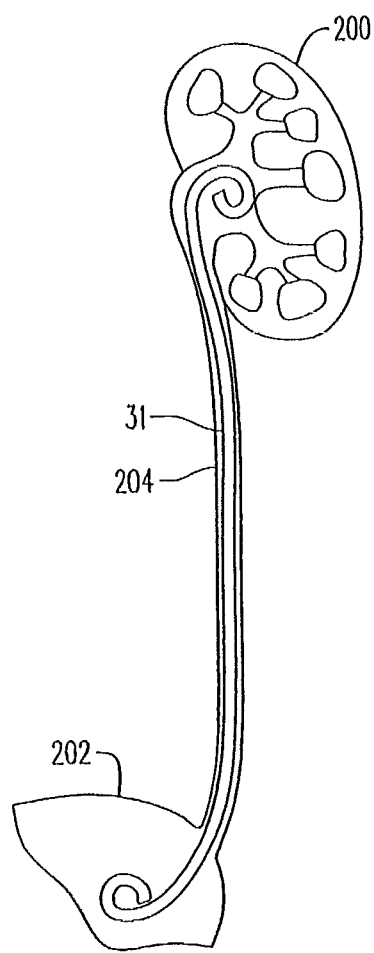
FIG. 12 is a schematic illustration of the elongated member shown in FIG. 11 serving as a ureteral stent extending between the kidney and the bladder.

FIGS. 10-12 illustrate another variation on the calculus removing/retrieving device described above. The calculus removing/retrieving device 30' is similar to the calculus removing/retrieving device 30 described above, except that a distal end 35 of the elongated member 31 is extended and possesses an open distal end 37. In addition, the proximal end portion of the elongated member 31 is configured so that the proximal-most end portion (operation portion) 33 is separable from the remainder of the elongated member 31 by way of a separable connector 39. The operation portion or proximal-most end portion 33 of the elongated member 31 is the part that is grasped and operated by the operator or medical professional.

A proximal end portion of the elongated member 31 and the proximal-most end portion (operation portion) 33 are connected by the separable connector 39 temporarily. That is, the separable connector 39 is a temporary connector. By way of example, the separable connector 39 can consist of weak fusion splicing or fitting parts (e.g., convex and concave). If the cross-sectional surface of the remainder of the elongated member 31 at the separable connector 39 side is forced in the forward direction toward the kidney by a pusher force existing in the proximal-most end portion (operation portion) 33 additional lumen, the elongated member 31 and the proximal-most end portion (operation portion) 33 can be separated rather easily.

In use, the calculus removing/retrieving device 30' is introduced into the ureter 204 in a manner similar to that described above (e.g., by way of the urethra and the bladder, and with or without the aid of a guide wire 62 and/or the ureteroscope 64). By virtue of the open distal end 37, the calculus removing/retrieving device 30' can serve as a ureteral stent or drainage tube prior to carrying out the medical procedure. That is, after the calculus removing/retrieving device 30' is positioned in the ureter 204 at the intended or desired location, the open ends of the calculus removing/retrieving device 30 creates or allows urinary flow through the calculus removing/retrieving device 30'. Urinary flow can thus continue while waiting to begin the medical procedure or operation (i.e., while waiting to begin flushing or washing with the liquid).

In addition, using the calculus removing/retrieving device 30' shown in FIG. 10, after the calculus removal/retrieval method is carried out as described above, the proximal-most end portion or operation portion 33 of the elongated member 31 can be separated from the remainder of the elongated member 31 at the separable connector 39. Following this separation, the proximal end portion of the elongated member 31 is open and positioned in the bladder 202, while the open distal end portion 35 remains positioned in the renal pelvis (kidney). Thus, following the medical procedure or operation to remove/retrieve the calculus, the elongated member 31 remains in place and operates as a drainage tube or ureteral stent that maintains urinary flow. Thus, this embodiment of the calculus removing/retrieving device 30 illustrated in FIGS. 10-12 provides a mechanism for maintaining urinary flow both before and after the calculus removing/retrieving procedure.

Figure 13:
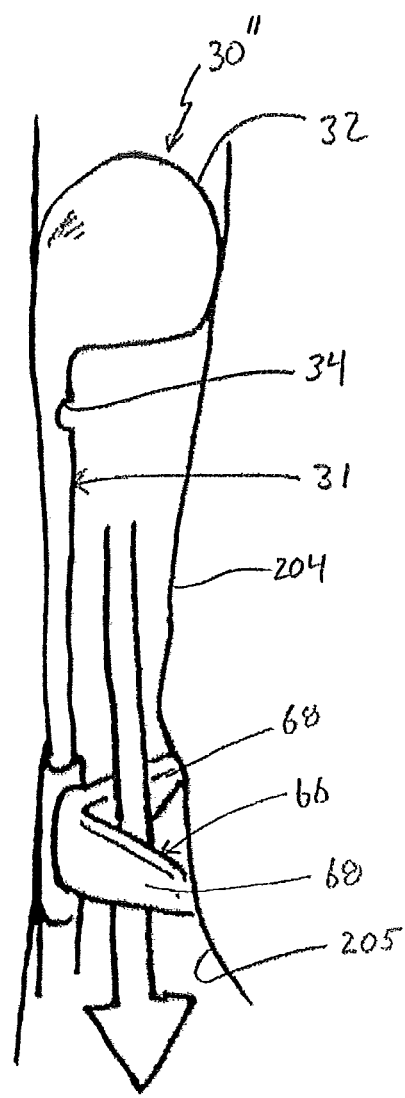
FIG. 13 is a schematic illustration of another embodiment of the calculus removing/retrieving device disclosed here by way of example and positioned in a ureteral lumen.
Figure 14:
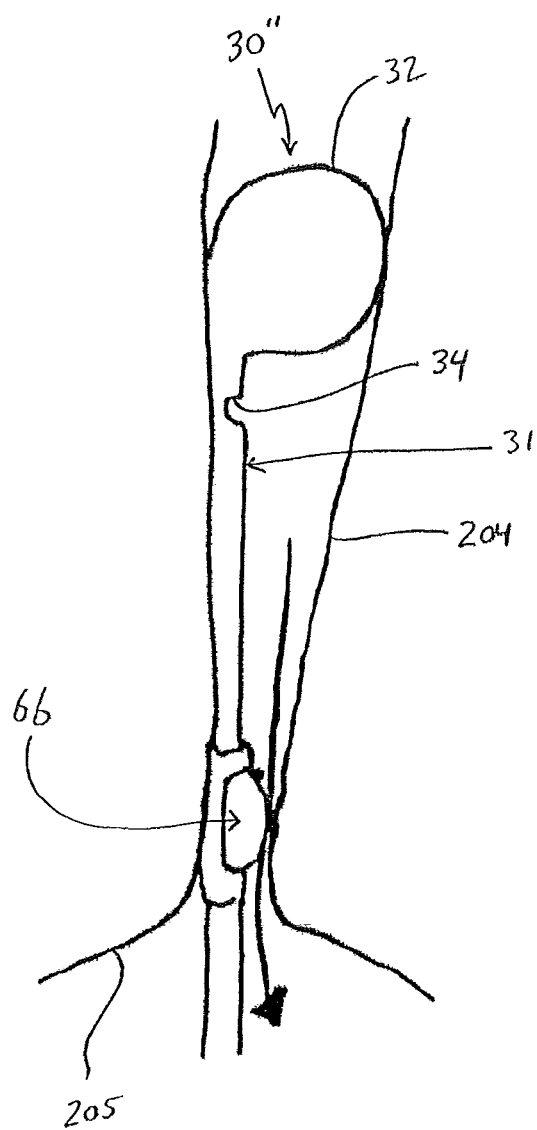
FIG. 14 illustrates the calculus removing/retrieving device shown in FIG. 13 depicting a different operational aspect of the device.

FIGS. 13 and 14 illustrate calculus removing/retrieving devices representing other examples of the device (and associated method) disclosed here. These embodiments of the calculus removing/retrieving device are the same as described above and illustrated in FIG. 3, except that the device is outfitted with a ureter wall pushing element to maintain a space or flow path for the fluid (liquid) discharged from the calculus removing/retrieving device as well as the calculus being washed away by the fluid. In the embodiment illustrated in FIG. 13, the calculus removing/retrieving device 30" includes a ureter wall pushing element 66 in the form of two spaced apart projections 68 affixed to the elongated member 31 and projecting away from the elongated member 31 into direct contact with the inner surface of the ureteral wall surrounding the ureteral lumen 205. The pushing element 66 is configured to be enlarged and reduced in size (expanded and contracted). In the illustrated embodiment disclosed by way of example, the pushing element 66 is an inflatable balloon in the same way of the ureter plug part 32. Through an additional lumen terminated at the pushing element 66 in the elongated member 31, the pushing element 66 is expanded (inflated) by introducing the fluid into an interior space of the pushing element 66, and the pushing element 66 is contracted (deflated) by allowing the fluid to empty from the ureter plug part 32. The fluid can be water, air, contrast medium, etc. The pushing element 66 has different characteristics from the ureter plug part 32; in the expanded state, the projections 68 are more shaped (elongated) and more rigid than the ureter plug part 32. FIG. 14 illustrates the contracted or deflated state of the pushing element 66.

The ureter wall pushing element 66 is beneficial in that it helps ensure that adequate space exists for flow of the flushing fluid which is generally illustrated by the arrow in FIG. 13. That is, the ureter wall pushing element 66 provides a flow path for the fluid (liquid) discharged from the calculus removing/retrieving device as well as the calculus being washed away by the flushing/washing fluid. The ureter wall pushing element 66 is especially helpful in this regard with respect to the narrowed ureter lumen such as UBJ 212.

Figure 15A:
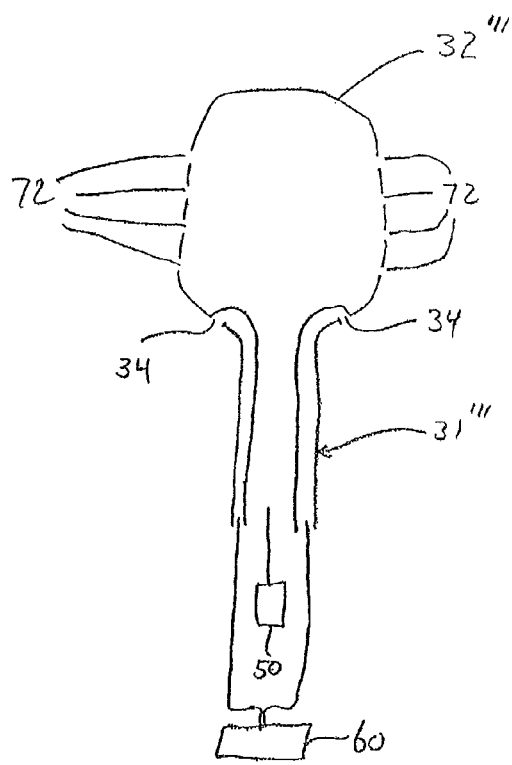
FIG. 15A is a schematic illustration of another embodiment of the elongated member disclosed here by way of example that includes an aspiration part.
Figure 15B:
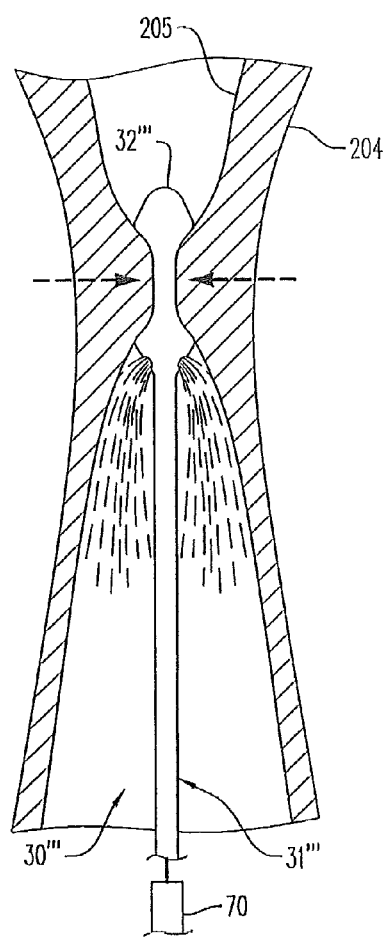
FIG. 15B is a schematic illustration of the elongated member shown in FIG. 15A aspirating a ureteral lumen.

FIGS. 15A and 15B illustrate a calculus removing/retrieving device representing another example of the device and associated method disclosed here. In the earlier embodiments of the calculus removing/retrieving device, the ureteral plug part 32 is configured to expand into contact with the lumen 205 of the ureter 204. This version of the calculus removing/retrieving device 30''' differs in that the ureteral plug part 32'' is configured to draw or pull, through suction or vacuum, the inner surface or wall of the ureteral lumen 205 of the ureter 204 towards and into contact with the ureteral plug part 32'''. FIG. 15A illustrates an example of the configuration of the ureteral plug part 32'''. The distal end portion of the elongated member 31''' is provided with a series of through holes or openings 72 which communicate with the interior of the elongated member 31'''. The interior of the ureteral plug part 32''' is connected to a suction source or vacuum source. In the illustrated embodiment, the vacuum or suction source is the syringe illustrated in FIG. 5. In the embodiment discussed above and illustrated in FIG. 5, the plunger 52 is pushed in the forward direction to inflate the ureteral plug part 32. In this embodiment, the plunger 52 is pulled in the rearward direction after the syringe is connected to the end of the elongated member 31''' to create a vacuum or suction that draws the inner surface of the ureteral lumen 205 towards and into direct contact with the outer surface of the ureteral plug part 32''' as illustrated in FIG. 15B. This embodiment thus provides an alternative way for occluding or closing-off the ureteral lumen 205 in the ureter 204. The ureteral plug part 32''' operates as an aspiration port.

The embodiment described above uses a syringe as a vacuum or suction source. But other vacuum or suction sources can be used.

Figure 16:
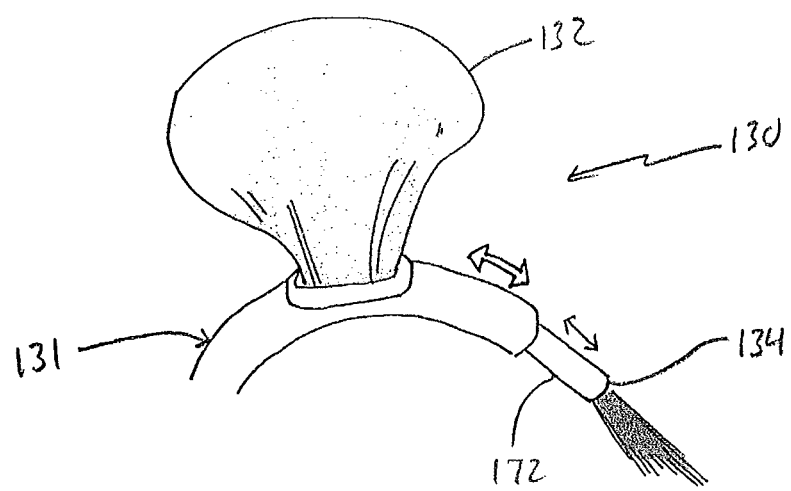
FIG. 16 is a schematic illustration of another embodiment of the elongated member disclosed here by way of example, wherein the calculus removing/retrieving device is specifically configured for use in the renal pelvis.

FIGS. 16 and 17 illustrate a calculus removing/retrieving device representing a further example of the device and associated method disclosed here. This embodiment has particularly useful applications for removing/retrieving calculus located in the renal pelvis (kidney). Generally speaking, the calculus removing/retrieving device 130 is configured to occlude or cover one part of the renal pelvis, and at the same time deliver or discharge washing or flushing fluid (liquid) to the remaining part of the renal pelvis to wash or flush away the calculus located in the other uncovered part of the renal pelvis.

Referring to FIG. 16, the calculus removing/retrieving device 130 includes an elongated member (main body) 131 and a tubular member or catheter 172 provided with the irrigation port or irrigation nozzle 134. The elongated member or main body 131 possesses a lumen open at both ends, and the tubular member 172 is axially movable within the lumen of the elongated member 131. The tubular member 172 also includes a lumen extending throughout the tubular member and open at both ends. In the illustrated embodiment disclosed by way of example, the irrigation port or irrigation nozzle 134 is the open distal end of the tubular member 172. The lumen in the tubular member 172 is connected to a fluid source, an example of which is the fluid source 60 illustrated in FIG. 3.

The lumen in the elongated member 131 (i.e., the space between the outer surface of the tubular member 172 and the inner surface of the elongated member 131) communicates with the interior of an expandable and contractible renal cover part 132 which is fixed to the elongated member 131.

The renal cover part 132 serves as an occluding means for occluding a portion of the renal pelvis as described in more detail below.

Figure 5:
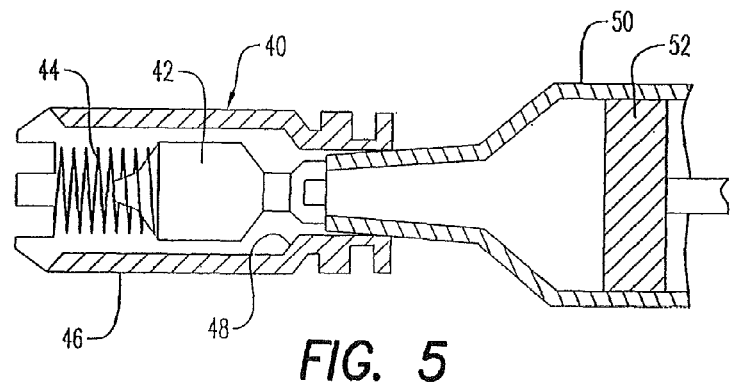
FIG. 5 is a cross-sectional view of the check valve shown in FIG. 4, with the distal portion of a syringe moving the check valve to the open position.

The lumen in the elongated member 131 is connected to a fluid source like the syringe 50 illustrated in FIG. 5. A check valve similar to that illustrated in FIGS. 3-6 can be employed to control the introduction of the fluid (e.g., air/gas) into the expandable/contractible renal cover part 132. The syringe 50 and the check valve also allow the fluid to be discharged from the renal cover part 132 as explained above. In the illustrated example, the expandable/contractible renal cover part 132 is an expandable balloon which expands (inflates) when fluid is introduced into the balloon and contracts (deflates) when fluid is expelled from the balloon.

An example of a method for retrieving/removing calculus from a renal pelvis using the calculus removing/retrieving device 130 illustrated in FIG. 17 is as follows. The calculus removing/retrieving device 130 is inserted into the body (e.g., by way of the urethra), passed through the bladder 202, and moved along the ureter 204 until entering the renal pelvis. Throughout this movement of the calculus removing/retrieving device 130 and introduction to the renal pelvis, the renal cover part 132 is in a deflated/contracted condition, and fluid is not discharged from the irrigation port or irrigation nozzle 134. After positioning the renal cover part 132 in the renal cavity, the renal cover part 132 is expanded or inflated to occlude or cover a part of the renal pelvis as generally illustrated in FIG. 17. After the one part of the renal pelvis is covered or occluded by the expanded renal cover part 132, fluid is discharged from the irrigation port or nozzle 134 and is directed at the other part of the renal pelvis that is not covered or occluded by the renal cover part 132. This fluid that is discharged from the irrigation port 134 washes out or flushes the uncovered part of the renal pelvis, taking with it the calculus. The calculus 300 and the fluid are then washed away or flushed-out by way of the ureter 204.

As a part of carrying out this operation, the irrigation port 134 can be pointed at the uncovered portion of the renal pelvis. This directed approach can help facilitate the flushing or washing-out of the calculus.

It is also possible as a part of this medical procedure to use lithotripsy on the calculus located in the renal pelvis before covering a part of the renal pelvis by inflating the renal cover part 132. In this case, lithotripsy is preferably carried out before introducing the renal cover part 132 into the renal pelvis.

The calculus removing/retrieving device 130 illustrated in FIG. 16 can be delivered to the renal pelvis using a ureteral access sheath and a ureteroscope, preferably a flexible ureteroscope. Here, the ureteral access sheath is first inserted into the living body and then the device 130 is inserted into the ureteroscope, and then the ureteroscope is inserted into the ureteral access sheath. The ureteral access sheath is introduced into the living body (for example by way of the urethra) and is advanced to a position where the tip end of the ureteral access sheath is located beyond (i.e., at the upper part or proximal part) the ureteropelvic junction. This is favorable positioning to help maintain or keep the flexibility of the tip end of the ureteroscope. The ureteroscope is used to visually observe the progress or movement of the calculus removing/retrieving device 130 towards the renal pelvis. Once the calculus removing/retrieving device 130 is properly positioned in the renal pelvis, the ureteroscope can be pulled back outside the body. The renal cover part 132 is then inflated to cover the one portion of the renal pelvis. In addition, the ureteroscope can be pulled back after the one part of the renal pelvis is covered or occluded by the expanded renal cover part 132. The fluid is discharged from the irrigation port or nozzle 134 to wash out the other part of the renal pelvis. The fluid and the calculus flow through the ureteral access sheath to outside the body.

FIGS. 18 and 19 illustrate an additional aspect of the calculus retrieving and removing method disclosed here and described above. This additional aspect involves subjecting the calculus to relatively small power to move or shift calculus (calculus-moving power or calculus-position changing power). This power may involve applying small impact waves generated when water flows from the irrigation port of the ureteroscope, or by vibrating or shaking the bed/table on which the patient is lying. The objective here is to move calculus from the one part of the renal pelvis to another part of the renal pelvis. This movement of the calculus from the one part of the renal pelvis to the other part of the renal pelvis is schematically illustrated in FIG. 18. The calculus is then collected in one part or region of the renal pelvis. The parts or region at which the calculus is collected is preferably the minor calyx. After the calculus is collected in the one part or region of the renal pelvis, the calculus removing/retrieving device is introduced into the renal pelvis, and the one part of the renal pelvis from which the calculus was removed or evacuated is covered by the inflated renal cover part 132 as illustrated in FIG. 19. The uncovered part of the renal pelvis is then washed or flushed by introducing fluid (liquid) into the renal pelvis through the irrigation port 134 as described above. Employing this additional aspect illustrated in FIGS. 18 and 19 improves the efficiency of the calculus removal/retrieval operation in that most or all of the calculus is moved to the area or region of the renal pelvis that is flushed-out by the fluid delivered from the irrigation port or nozzle 134.

FIG. 19 illustrates an additional aspect associated with this embodiment of the calculus retrieval/removal device and method. As shown in FIG. 19, a pressure sensor 145 is attached to the calculus removing/retrieving device 130, specifically the elongated member 131. This pressure sensor 145 senses the pressure in the renal pelvis. The pressure sensor 145 is connected to a control unit 146 which controls operation of the calculus removing/retrieving device 130, including the discharge of the fluid out of the irrigation nozzle 134. When information provided by the pressure sensor 145 indicates that the intra-renal pressure (i.e., the pressure inside the renal pelvis) is greater than a certain pressure (e.g., from 0.2 $mH_2O$ to 0.7 $mH_2O$, more favorable, from 0.3 $mH_2O$ to 0.5 $mH_2O$), the control unit 147 can alert the high intra-renal pressure to the physician and/or stop discharging additional fluid (water) into the renal pelvis.

Figure 20:
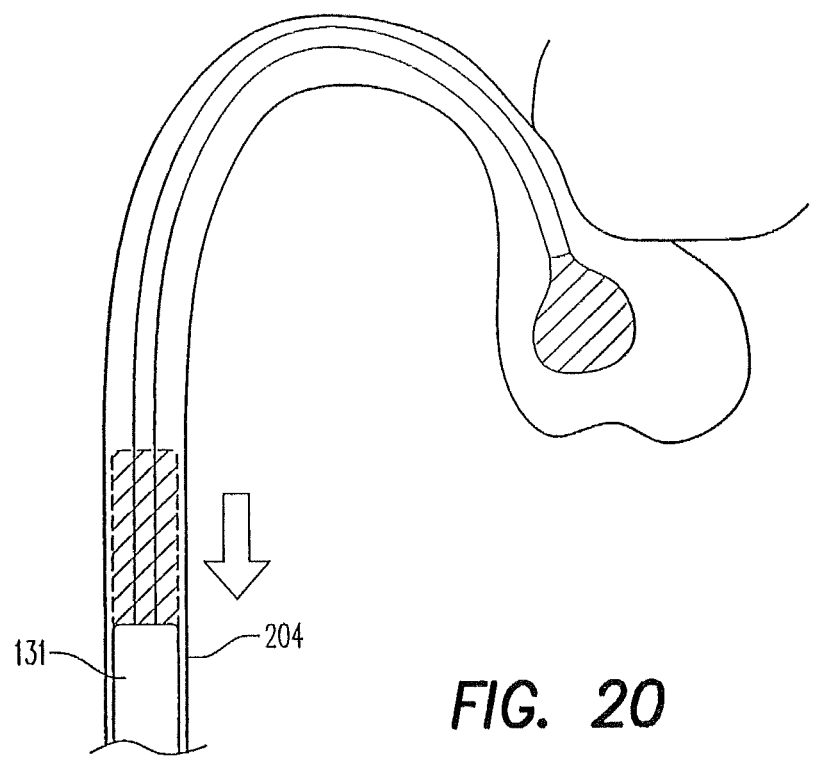
FIG. 20 is a schematic illustration of the procedure that the volume of "pulling back the ureteroscope" and "additional pouring irrigation water" is continuously adjusted to be equal (i.e., the same) to avoid a rise or increase in the intra-renal pressure.

FIG. 20 illustrates another aspect of the disclosure here. First, the renal cover part 132 is inflated to cover the one portion of the renal pelvis. Then the ureteroscope is pulled back, and simultaneously fluid is discharged from the irrigation port or nozzle 134 to wash out the other part of the renal pelvis. As shown in FIG. 20, to avoid a rise of the intra-renal pressure, the volume of "pulling back the ureteroscope" represented by the shaded portion near the arrow in FIG. 20 and the "additional pouring irrigation water" represented by the other shaded portion in FIG. 20, should be continuously adjusted as equal. Through this procedure, physician can see the calculus state by ureteroscope during washing out.

The calculus removing/retrieving device 130 shown in FIG. 16 can also be used to "rake" out the calculus or stones in a manner similar to that described above. For example, after the one part of the renal pelvis is covered or occluded by the expanded renal cover part 132, the fluid that is discharged from the irrigation port 134 washes out or flushes the uncovered part of the renal pelvis, taking with it the calculus. The calculus 300 and the fluid partially can be washed away or flushed-out by way of the ureter 204, but residues (residual calculi) exist in the ureter 204. To remove these residual calculi, the renal cover part 132 may be deflated or contacted, and moved rearwardly within the ureter 204 in the direction toward the bladder 202. Then the renal cover part 132 is re-expanded or re-inflated until the surface of the renal cover part 132 partially touches the ureter 204. The renal cover part 132 is moved in this way while the renal cover part 132 is in the expanded or inflated state so that the expanded or inflated renal cover part 132 pulls along or rakes the calculus or stones 300.

It is also possible to use the calculus removing/retrieving device 130 shown in FIG. 16 to "rake" out the calculus or stones in the ureteral access sheath when the ureteral access sheath is used. In this situation, the residual calculus 300 and the fluid exist in the ureteral access sheath the same as above. The calculus removing/retrieving device 130 is delivered to the lumen of the ureteral access sheath while the renal cover part 132 is deflated or contacted. After reaching the desired position in the ureteral access sheath lumen, the renal cover part 132 is expanded (inflated) and then pulled rearwardly within the ureteral access sheath lumen to rakeout calculus or stones in the ureteral access sheath lumen. In this variation, the extent to which the renal cover part 132 can be expanded or inflated will be dictated by the inner diameter of the ureteral access sheath lumen.

According to another aspect of the disclosure here, when the calculus removing/retrieving device 130 shown in FIG. 16 is used with a ureteroscope, the amount of pull-back or rearward movement of the calculus removing/retrieving device 130 is controlled according to the amount of water being discharged into the renal pelvis. As explained above, it is possible to use a ureteroscope to visually observe the movement of the calculus removing/retrieving device 130 into the renal pelvis. When the calculus removing/retrieving device 130 reaches the desired position in the renal pelvis, the ureteroscope can be pulled-back before the convection-producing discharge of the fluid into the renal pelvis or the ureteroscope can be held at its current position. In the latter case, as the fluid (wash-out fluid) is discharged into the renal pelvis, the ureteroscope is pulled-backward, accompanied by the calculus/stones and the wash-out fluid. This pull-back of the ureteroscope is controlled so that the volume of the pulling-back of the ureteroscope equals the volume of fluid (water) being discharged from the irrigation port 134.

FIGS. 21-24 illustrate a calculus removing/retrieving device representing a further example of the device and associated method disclosed here. This embodiment of the calculus removing/retrieving device 330 includes an elongated member 331 provided with an irrigation port or nozzle 334, representing an example of an outlet. An irrigation lumen 336 extends along the elongated member 331. The irrigation lumen 336 communicates with the irrigation port or nozzle 334 and also possesses an open proximal end. A plunger 376 is movably positioned in the irrigation lumen 336 to slide along the length of the irrigation lumen. The plunger includes a rubber gasket or plug 378 fixed to the plunger 376 so that the rubber gasket 378 moves together with the plunger 376 as a unit. The gasket 378 fluid-tightly engages the inner surface of the irrigation lumen 336.

The calculus removing/retrieving device 330 also includes a suction port 380, representing an example of an inlet. In the illustrated embodiment shown in FIGS. 21 and 22, the suction port 380 is positioned proximally of the irrigation port 334. A check valve 382 (one-way valve) closes the irrigation port 334, while another check value 384 (one-way valve) closes the suction port 380. The check valve 382 allows fluid to be discharged from the irrigation lumen 336 to outside the device as illustrated by the arrow 375 in FIG. 21. On the other hand, the check valve 382 prevents the fluid from flowing into the irrigation lumen 336 in the direction opposite the arrow 375.

Figure 21:
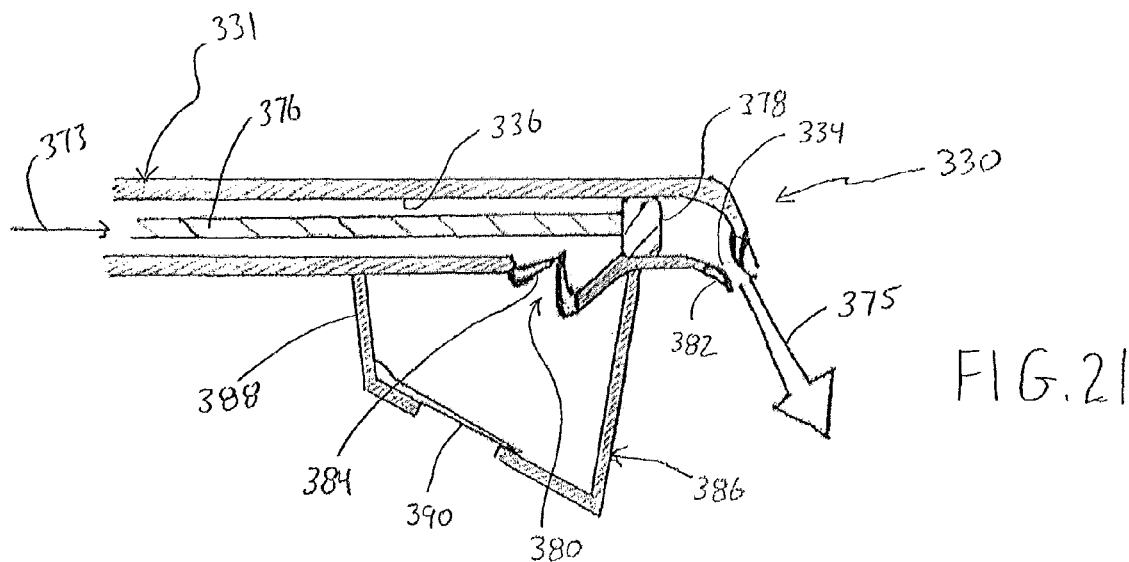
FIG. 21 is a schematic cross-sectional view of a calculus removing/retrieving device according to a further embodiment disclosed here by way of example, wherein the calculus removing/retrieving device has particular application for use in a renal pelvis.

Referring to FIG. 21, when the plunger 376 is pushed in the forward direction indicated by the direction of the arrow 373 in FIG. 21, fluid (liquid) in the irrigation lumen 336 and positioned ahead of the gasket 378 (i.e., on the right side of the gasket 378 in FIG. 21) is discharged out through the irrigation port 334 by way of the check valve 382. The check valve 382 is configured to permit flow in the direction of the arrow 375 while preventing flow in the direction opposite the arrow 375.

Figure 22:
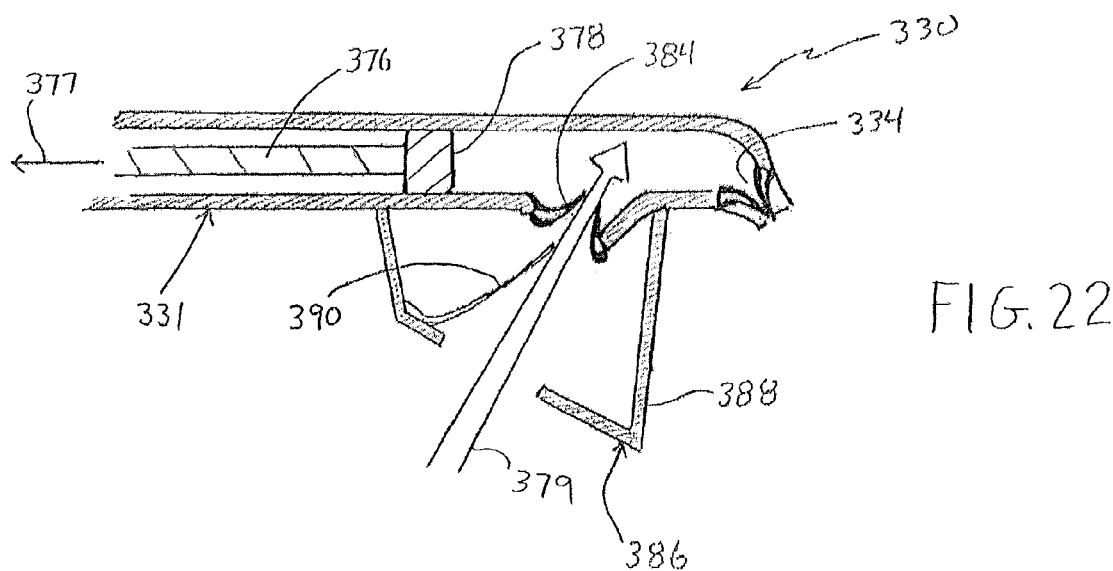
FIG. 22 is a schematic illustration of the calculus removing/retrieving device shown in FIG. 21 depicting a different operational aspect of the device.

Referring to FIG. 22, when the plunger is pulled rearwardly in the direction indicated by the direction of the arrow 377 in FIG. 22, a suction or vacuum is created on the distal side of the gasket 378 (i.e., the right side of the gasket with reference to FIGS. 21 and 22) to draw fluid and calculus into the lumen 336 by way of the check valve 384. The check valve 384 is configured to permit flow in the direction of the arrow 379 while preventing flow in the direction opposite the arrow 379.

The calculus removing/retrieving device 330 shown in FIGS. 21 and 22 also includes a retrieval part 386 generally in the form of a housing or enclosure 386. A check valve 390 is provided in the enclosure 388 to separate the interior of the enclosure 386 and the exterior of the enclosure. When open, the check valve 390 permits communication between the interior of the enclosure 386 and the exterior of the enclosure. The check valve 390 is similar to the check valve 384, but the check valve 390 can be opened more easily than the check valve 384. In other words, the closing power of the check valve 390 is less than the closing power of the check valve 384. Thus, when the plunger is pulled rearwardly in the direction of the arrow 377 in FIG. 22, the check valve 390 is opened more widely and/or is opened for a longer period of time than the check valve 384. The check valve 390 permits fluid and calculus (kidney stones or stone fragments) to pass through into the enclosure 388, but the check valve 384 permits only the fluid to pass through into the lumen 336.

Figure 23:
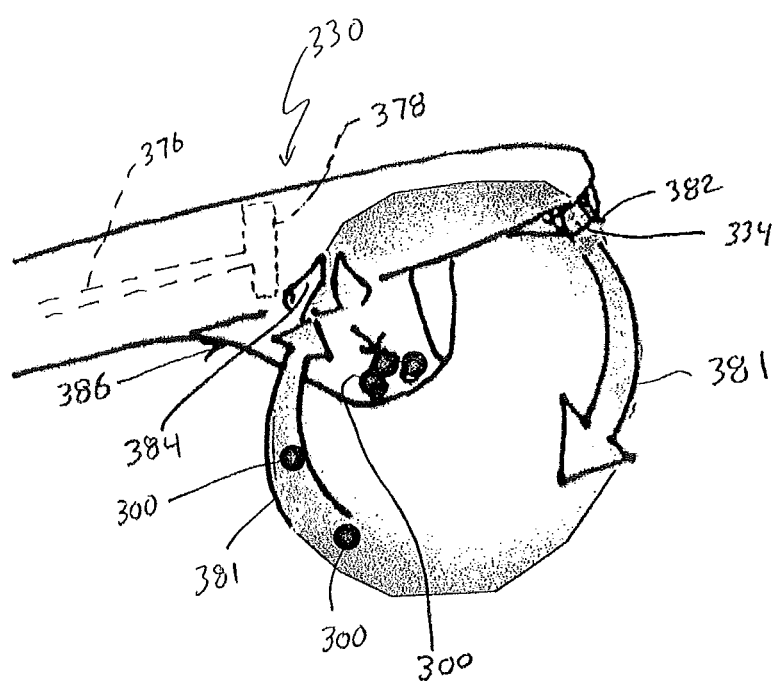
FIG. 23 is a schematic illustration of the calculus removing/retrieving device shown in FIGS. 21 and 22, depicting the convection produced during operation of the device.

FIG. 23 generally illustrates operational aspects associated with use of the calculus removing/retrieving device 330. The irrigation lumen 336 that communicates with the irrigation port or nozzle 334 is filled with a fluid (e.g., a liquid such as water, saline, etc.) and then the plunger/gasket 378 is positioned inside the irrigation lumen 336 and moved in the forward direction toward the irrigation port 334. As the plunger 376 moves in the forward direction indicated by the arrow 373, the fluid inside the irrigation lumen is discharged through the irrigation port 334 by way of the check valve 382 and creates convection in the renal pelvis as schematically indicated by the arrow 381 in FIG. 23. This convection is beneficial because when the calculus removing/retrieving device is positioned in the renal pelvis, the convection created by the fluid discharged through the irrigation port 334 stirs-up the calculus or stone fragments that are present in the renal pelvis. That is, the calculus is lifted-off of the surface of the renal pelvis and is suspended in the convection, thus helping to facilitate the retrieval of the calculus. During this forward movement of the plunger 376, the check valve 382 is open while the check valve 384 at the suction port and the check valve 390 at the retrieval part 386 remain closed.

Figure 24:
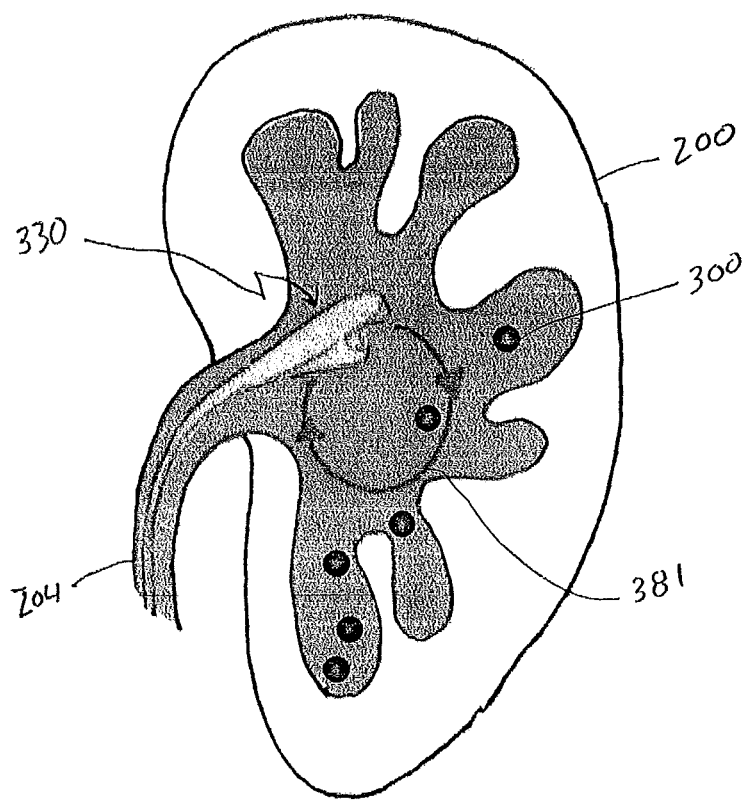
FIG. 24 illustrates the calculus removing/retrieving device shown in FIGS. 21 and 22 positioned in a renal pelvis and producing convection.

After the plunger 376 has reached the end of its forward stroke, movement of the plunger 376 stops and the check valve 382 automatically closes. Next, the plunger 376 is pulled in the rearward direction to retrieve the calculus that has been stirred-up or lifter by the fluid convection. This rearward movement of plunger 376 in the direction of the arrow 377 causes the check valve 382 to close. As the plunger 376 is pulled in the rearward direction, a vacuum or suction is created in front of the gasket 378. This causes the check valve 384 to open, and causes the check valve 390 to be wide-opened (more widely-open than the check valve 384) so that fluid and calculus or stones in the renal pelvis flow through the check valve 390 and enter the enclosure 388. The calculus or stones 300 which have passed though the check valve 390 tend to remain in the enclosure 388 and fall toward the bottom of the enclosure due to their weight, whereas the fluid passing through the check valve 390 and entering the enclosure 388 is drawn through the open check valve 384, enters the inside of the irrigation lumen 336. If the plunger 376 is pushed and pulled continuously, a relatively stable convection can be generated in the renal pelvis FIG. 24 schematically illustrates the calculus removing/retrieving device 330 positioned in the renal pelvis of the kidney 200. As described previously, the calculus removing/retrieving device can be inserted through the urethra, advanced through the bladder and along ureter 204 where it enters the renal pelvis. Once the calculus removing/retrieving device 330 is properly positioned in the renal pelvis, the plunger 376 is moved in the forward direction to discharge fluid out of the irrigation lumen 336, through the irrigation port or nozzle 334 and into the renal pelvis to create fluid convection as described above. FIG. 24 illustrates the way that the fluid convection lifts and suspends the calculus 300. During the discharge of the fluid though the irrigation port 334, the check valve 382 is open while the check valve 384 and the check valve 390 remain closed. After the plunger reaches the end of its forward stroke, the plunger is pulled in the rearward direction to cause fluid and calculus/stone fragments to be drawn through the check valve 390 and into the enclosure 388. The calculus or stone fragments collect in the enclosure 388 where they gather and are held by virtue of their weight. On the other hand, the fluid that is drawn through the check valve 390 passes through the check valve 384 and continues to be drawn along the irrigation lumen 336. During the rearward movement of the plunger, the check valve 384 and the check valve 390 are open while the check valve 382 remains closed.

As in the embodiments described above, it is possible to insert the calculus removing/retrieving device 330 into the living body using a ureteroscope, preferably a flexible ureteroscope. The calculus removing/retrieving device 330 is introduced into the instrument channel of the ureteroscope and is advanced to the renal pelvis while being observed through operation of the ureteroscope.

As an alternative to the configuration of the calculus removing/retrieving device 330 shown in FIGS. 21 and 22, it is possible to do away with the retrieval part 386 of the calculus removing/retrieving device 330. In this alternative, the ureteroscope is used in the manner described above to visually observe the forward movement of the calculus removing/retrieving device toward the renal pelvis. Once the calculus removing/retrieving device is appropriately positioned in the removing/retrieving device, the ureteroscope is pulled back to the ureteropelvis junction 208 (shown in FIG. 1) or into the ureter 204 (shown in FIG. 1). This creates a space between the distal end of the ureteroscope and the ureteral inner wall. The calculus/stone fragments are then collected in this space formed by the tip end of the ureteroscope and the ureteral inner wall when the ureteroscope is pulled back, instead of the retrieval part 386. The calculus/stone fragments together with the fluid enter this space and flow along the ureter to the bladder or outside the body. As explained above, a continuous pushing and pulling procedure is necessary to generate the stable convection in the renal pelvis and maintain the renal pelvis capacity.

Figure 25A:
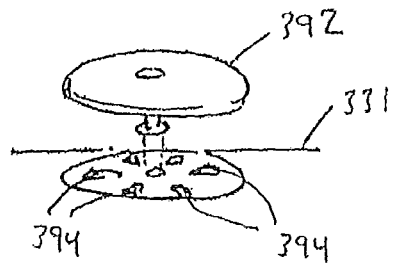
FIGS. 25A-25C are illustrations of a rubber seal check valve that can be used as an example of the check valve for the calculus removing/retrieving device shown in FIGS. 21 and 22.
Figure 25B:
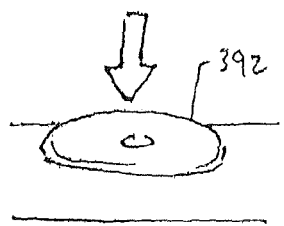
Figure 25C:
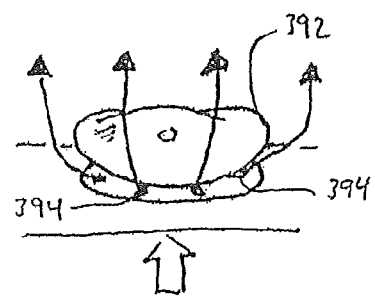

FIGS. 25A and 25C illustrate a rubber seal check valve which can be used as a specific form of the check valve 382, 384 in the calculus removing/retrieving device 330. The rubber seal check valve includes a rubber element 392 secured to the elongated member 331. The rubber element 392 covers a plurality of holes or through openings 394 in the elongated member 331. The rubber element 392 is secured to the elongated member 331 in any appropriate way so that the rubber element 392 normally covers the holes or through openings 394. When pressure is applied from the side opposite the rubber element 392, the rubber element 392 is lifted as shown in FIG. 25C to allow fluid to discharge or pass through the holes 394.

Thus, if the rubber seal check valve is used for the valve 382 shown in FIGS. 21 and 22, the valve would take the position shown in FIG. 25C when the plunger 376 is pushed in the forward direction and would take the position shown in FIG. 25B when the plunger 376 is pulled in the rearward direction. If the rubber seal check valve is used for the valve 384 shown in FIGS. 21 and 22, the valve would be in the position shown in FIG. 25B when the plunger 376 is moved in the forward direction and would move to the position shown in FIG. 25C when the plunger 376 is pulled in the rearward direction.

Figure 26:
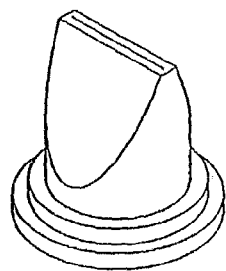
FIG. 26 illustrates duck bill-type check valves that can be used as an example of the check valve for the calculus removing/retrieving device shown in FIGS. 21 and 22.

FIG. 26 illustrates known duck bill-type valves which can be used as another specific form of the check valve 382, 384 in the calculus removing/retrieving device 330. If the duck bill-type valves is used for the valve 382 shown in FIGS. 21 and 22, the narrowed mouth of the duck bill-type valve would open when the plunger 376 is pushed in the forward direction and would return to the closed position when the plunger 376 is pulled in the rearward direction. If the duck bill-type valve is used for the valve 384 shown in FIGS. 21 and 22, the narrowed mouth of the duck bill-type valve would open when the plunger 376 is pulled in the rearward direction and would return to the closed position when the plunger 376 is pushed in the forward direction.

Figure 27:
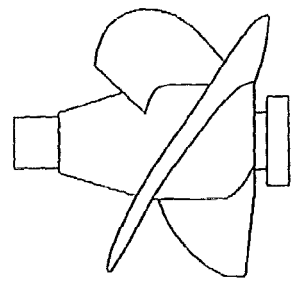
FIG. 27 is an illustration of an impeller.

FIG. 27 illustrates an example of an impeller which can also be employed in the calculus removing/retrieving device 330. Instead of the plunger 376 pushing and pulling action (movement) in the lumen 336 equipped with the oppositely-oriented check valve arrangement, mechanically rotating the impeller can create the objective convection in the renal cavity.

The detailed description above describes a device and method for retrieving/removing calculus from parts of a living body such as the ureter and the renal pelvis. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A calculus retrieving device for removing calculus in a renal pelvis, the calculus retrieving device comprising:
an elongated member possessing a longitudinal extent and including a lumen extending along the longitudinal extent of the elongated member, the elongated member possessing a distal end portion;
a plunger positioned in the lumen of the elongated member and axially movable in a forward direction and a rearward direction along the lumen of the elongated member;
an enclosure fixed to the elongated member at a distal end portion of the elongated member so that the elongated member and the enclosure are movable together as a unit, the elongated member and the enclosure together being sized to be positioned in a renal pelvis;
an outlet in selective communication with the lumen and through which fluid in the lumen is discharged into the renal pelvis during axial movement of the plunger in the forward direction;
an inlet in selective communication with the lumen and through which fluid in the renal pelvis is drawn into the lumen during axial movement of the plunger in the rearward direction; and
the enclosure enclosing an interior configured to receive the calculus in the renal pelvis that is drawn toward the inlet together with the fluid in the renal pelvis during the axial movement of the plunger in the rearward direction.

2. The calculus retrieving device of claim 1, further comprising a gasket fixed to the plunger so that the plunger and the gasket move together as a unit.

3. The calculus retrieving device of claim 1, further comprising a sealing part fixed to the plunger so that the plunger and the sealing part move together as a unit, and wherein the sealing part fluid-tightly engages an inner surface of the elongated member surrounding the lumen so that the axial movement of the plunger and the sealing part in the rearward direction creates suction in the lumen that draws the fluid in the renal pelvis into the lumen.

4. The calculus retrieving device of claim 1, wherein the enclosure is configured to allow the fluid in the renal pelvis to enter the interior of the enclosure, to pass through the interior of the enclosure and to exit the interior of the enclosure while the calculus remains in the interior of the enclosure.

5. The calculus retrieving device of claim 1, wherein the outlet is configured to allow fluid to pass through the outlet in only one direction and the inlet is configured to allow fluid to pass through the inlet in only one direction.

6. The calculus retrieving device of claim 1, further comprising a check valve at the outlet that prevents fluid in the renal pelvis from entering the lumen by way of the outlet.

7. The calculus retrieving device of claim 1, further comprising a check valve at the inlet that prevents fluid in the lumen to be discharged out of the lumen by way of the inlet.

8. The calculus retrieving device of claim 1, wherein the inlet is located between the interior of the enclosure and the lumen so that the fluid in the renal pelvis which is drawn into the lumen during the axial movement of the plunger in the rearward direction must enter the interior of the enclosure and pass through the interior of the enclosure before passing through the inlet and entering the lumen.

9. The calculus retrieving device of claim 1, further comprising a valve provided on the enclosure at a position spaced from the inlet, the valve being configured to permit the fluid in the renal pelvis to pass through the valve and enter the interior of the enclosure during the axial movement of the plunger in the rearward direction.

10. The calculus retrieving device of claim 9, wherein the valve is a check valve that permits fluid to enter the interior of the enclosure during the axial movement of the plunger in the rearward direction and that prevents fluid in the interior of the enclosure from being discharged to the renal pelvis by way of the check valve.

11. The calculus retrieving device of claim 9, wherein the interior of the enclosure is positioned between the inlet and the valve so that during the axial movement of the plunger in the rearward direction the fluid in the renal pelvis passes through the valve and enters the interior of the enclosure before passing through the inlet.

12. A calculus retrieving device for removing calculus in a renal pelvis, the calculus retrieving device comprising:
an elongated member;
a retrieval part fixed to the elongated member so that the elongated member and the retrieval part are movable together as a unit, the elongated member and the retrieval part together being sized to be positioned in the renal pelvis;
the elongated member including a lumen in which is produced a discharge force to discharge fluid in the lumen out of the elongated member and into the renal pelvis and in which is produced a suction force to draw fluid into the lumen from the renal pelvis;
an outlet in selective communication with the lumen in the elongated member and through which fluid in the lumen is discharged into the renal pelvis by the discharge force in the lumen of the elongated member;
an inlet in selective communication with the lumen in the elongated member and through which fluid in the renal pelvis is drawn into the lumen by the suction force in the lumen of the elongated member; and
the retrieval part including an interior that communicates with the lumen and that communicates with the renal pelvis when the calculus retrieving device is in the renal pelvis, the interior of the retrieving part being configured to receive the calculus in the renal pelvis when the suction force is produced in the lumen of the elongated member, the retrieval part being configured to allow the fluid which enters the interior of the retrieval part to pass through the interior of the retrieval part and exit the interior of the retrieval part while the calculus remains in the interior of the retrieval part.

13. The calculus retrieving device of claim 12, further comprising a sealing part positioned in the lumen in the elongated member and axially movable in the lumen in a direction toward a distal end of the elongated member to produce the discharge force and in a direction away from the distal end of the elongated member to produce the suction force.

14. The calculus retrieving device of claim 12, wherein the outlet is positioned distally of the inlet.

15. The calculus retrieving device of claim 12, further comprising a one-way valve at the outlet that prevents fluid in the renal pelvis from entering the lumen by way of the outlet.

16. The calculus retrieving device of claim 12, further comprising a one-way valve at the inlet that prevents fluid in the lumen from being discharged into the renal pelvis by way of the inlet.

17. The calculus retrieving device of claim 12, further comprising a check valve at the outlet that prevents fluid in the renal pelvis from entering the lumen by way of the outlet.

18. The calculus retrieving device of claim 12, further comprising a check valve at the inlet that prevents fluid in the lumen from being discharged into the renal pelvis by way of the inlet.

19. A calculus retrieving device for removing calculus in a renal pelvis, the calculus retrieving device comprising:
- an elongated member;
- a retrieval part fixed to the elongated member so that the elongated member and the retrieval part are movable together as a unit, the elongated member and the retrieval part together being sized to be positioned in the renal pelvis;
- the elongated member including a lumen in which is produced a discharge force to discharge fluid in the lumen out of the elongated member and into the renal pelvis and in which is produced a suction force to draw fluid into the lumen from the renal pelvis;
- an outlet in selective communication with the lumen in the elongated member and through which fluid in the lumen is discharged into the renal pelvis by the discharge force in the lumen of the elongated member;
- an inlet in selective communication with the lumen in the elongated member and through which fluid in the renal pelvis is drawn into the lumen by the suction force in the lumen of the elongated member;
- the retrieval part including an interior that communicates with the lumen and that communicates with the renal pelvis when the calculus retrieving device is in the renal pelvis, the interior of the elongated member retrieving part being configured to receive the calculus in the renal pelvis when the suction force is produced in the lumen of the elongated member; and
- a one-way valve provided on the retrieval part at a position spaced from the inlet so that the interior of the retrieval part is located between the inlet and the one-way valve.

20. The calculus retrieving device of claim 19, further comprising a check valve at the inlet configured to prevent fluid in the lumen from being discharged into the retrieval part by way of the inlet.

* * * * *